US012805997B2

(12) United States Patent
Kaur et al.

(10) Patent No.: US 12,805,997 B2
(45) Date of Patent: Nov. 24, 2026

(54) CONTROLLING THE SIZE OF 3D PRINTING HYDROGEL OBJECTS USING HYDROPHILIC MONOMERS HYDROPHOBIC MONOMERS, AND CROSSLINKERS

(71) Applicant: Lung Biotechnology PBC, Silver Spring, MD (US)

(72) Inventors: Aman Kaur, Manchester, NH (US); Isabel Arias, Manchester, NH (US); Barbara Nsiah, Manchester, NH (US); Luis Alvarez, Lexington, MA (US)

(73) Assignee: Lung Biotechnology PBC, Silver Spring, MD (US)

( * ) Notice: Subject to any disclaimer, the term of this patent is extended or adjusted under 35 U.S.C. 154(b) by 992 days.

(21) Appl. No.: 17/738,764

(22) Filed: May 6, 2022

(65) Prior Publication Data

US 2022/0370188 A1 Nov. 24, 2022

Related U.S. Application Data

(60) Provisional application No. 63/185,300, filed on May 6, 2021.

(51) Int. Cl.

| | |
|---|---|
| ***A61F 2/02*** | (2006.01) |
| ***A61L 27/16*** | (2006.01) |
| ***B33Y 10/00*** | (2015.01) |
| ***B33Y 70/00*** | (2020.01) |
| ***B33Y 80/00*** | (2015.01) |
| ***C09D 11/38*** | (2014.01) |
| ***C09D 133/08*** | (2006.01) |
| ***C09D 133/10*** | (2006.01) |

(52) U.S. Cl.

CPC ................ *A61F 2/02* (2013.01); *A61L 27/16* (2013.01); *C09D 11/38* (2013.01); *C09D 133/08* (2013.01); *C09D 133/10* (2013.01); *A61F 2210/0061* (2013.01); *B33Y 10/00* (2014.12); *B33Y 70/00* (2014.12); *B33Y 80/00* (2014.12)

(58) Field of Classification Search

CPC .... A61F 2/02; A61F 2210/0061; A61L 27/16; C09D 11/38; C09D 133/08; C09D 133/10; B33Y 10/00; B33Y 70/00; B33Y 80/00

See application file for complete search history.

(56) References Cited

U.S. PATENT DOCUMENTS

| | | | | |
|---|---|---|---|---|
| 5,645,581 | A | 7/1997 | Zurbrugg | |
| 6,174,929 | B1 * | 1/2001 | Hahnle ...................... | C08J 9/30 521/64 |
| 11,371,014 | B2 | 6/2022 | Miller et al. | |
| 11,597,915 | B2 | 3/2023 | Xu et al. | |
| 2008/0029392 | A1 * | 2/2008 | Makuska .............. | C08F 251/00 204/468 |
| 2009/0011486 | A1 | 1/2009 | Bettinger et al. | |
| 2010/0221304 | A1 | 9/2010 | Tan et al. | |
| 2013/0029030 | A1 | 1/2013 | Larsen | |
| 2014/0335496 | A1 | 11/2014 | Grego et al. | |
| 2017/0307598 | A1 | 10/2017 | Skardal et al. | |
| 2017/0354758 | A1 | 12/2017 | Deng et al. | |
| 2018/0002658 | A1 | 1/2018 | Miller et al. | |
| 2018/0243481 | A1 | 8/2018 | Martin et al. | |
| 2020/0040306 | A1 | 2/2020 | Xu et al. | |
| 2020/0179563 | A1 | 6/2020 | Bagley et al. | |
| 2020/0237520 | A1 | 7/2020 | Vaquette et al. | |
| 2020/0324021 | A1 | 10/2020 | Van Belleghem et al. | |
| 2020/0339925 | A1 | 10/2020 | Miller et al. | |
| 2020/0347167 | A1 | 11/2020 | Alli et al. | |
| 2021/0069378 | A1 | 3/2021 | Nelson et al. | |

FOREIGN PATENT DOCUMENTS

| | | | |
|---|---|---|---|
| CN | 105688279 | A | 6/2016 |
| CN | 107320780 | A | 11/2017 |
| CN | 110358006 | A | 10/2019 |
| CN | 112206074 | A | 1/2021 |
| DE | 10 2019 132 211 | B3 | 4/2021 |
| EP | 0 466 105 | A2 | 1/1992 |
| EP | 3 514 228 | A1 | 7/2019 |
| JP | 2018-036524 | A | 3/2018 |
| WO | WO-2005/105172 | A1 | 11/2005 |
| WO | WO-2016/154070 | A1 | 9/2016 |
| WO | WO-2017/031167 | A1 | 2/2017 |
| WO | WO-2017/040156 | A1 | 3/2017 |
| WO | WO-2017/066507 | A1 | 4/2017 |

(Continued)

OTHER PUBLICATIONS

Weigel et al. "Photopolymer formulations for SL printing hydrogel microstructures as swellable functional elements" in Proc. Of SPIE vol. 11637, pp. 1-13, Mar. 5, 2021, submitted by applicant in Form 1449. (Year: 2021).*

Fan et al., "Bio-printing cell-laden Matrigel-agarose constructs," Journal of Biomaterials Applications, 2016, 31(5):684-692.

Grigoryan et al., "Multivascular networks and functional intravascular topologies within biocompatible hydrogels," Science, May 3, 2019, 364(6439):458-464, with Supplementary materials (39 pages).

Huh et al., "Reconstituting Organ-Level Lung Functions on a Chip," Science, Jun. 25, 2010, 328(5986):1662-1668.

Kim et al., "Bio-ink Materials for 3D Bio-printing," Journal of International Society for Simulation Surgery, 2016, 3(2):49-57.

Ma et al., "A Novel Method for Preparing Poly(vinyl alcohol) Hydrogels: Preparation, Characterization, and Application," Industrial & Engineering Chemistry Research, Jun. 21, 2017, 56:7971-7976.

(Continued)

*Primary Examiner* — Blessing M Fubara
(74) *Attorney, Agent, or Firm* — Foley & Lardner LLP

(57) ABSTRACT

The present disclosure provides printable compositions comprising: about 1 weight percent (wt %) to about 40 wt % of one or more hydrophilic monomers; a swelling control agent selected from a hydrophobic monomer, a short chain crosslinker, or a combination thereof; about 0.01 wt % to about 2 wt % of a photo initiator; and 0 wt % to about 75 wt % of a vehicle comprising a protic solvent, by weight of the printable composition. The disclosure also includes methods of use and manufacture related to printable compositions.

16 Claims, 8 Drawing Sheets

(56) References Cited

FOREIGN PATENT DOCUMENTS

| | | | |
|---|---|---|---|
| WO | WO-2017/210298 | A1 | 12/2017 |
| WO | WO-2018/187372 | A2 | 10/2018 |
| WO | WO-2019/195256 | A1 | 10/2019 |
| WO | WO-2019/226710 | A8 | 11/2019 |
| WO | WO-2020/028720 | A1 | 2/2020 |
| WO | WO-2020/102260 | A1 | 5/2020 |
| WO | WO-2020/182987 | A1 | 9/2020 |

OTHER PUBLICATIONS

MilliporeSigma. https://www.sigmaaldrich.com/deepweb/assets/sigmaaldrich/marketing/global/images/technical-documents/articles/analytical-chemistry/purification/solvent-miscibility-table/solvent-miscibility-table.png. (Year: 2024).

Scarritt et al., "Re-endothelialization of rat lung scaffolds through passive, gravity-driven seeding of segment-specific pulmonary endothelial cells," Journal of Tissue Engineering and Regenerative Medicine, 2018 (May 7, 2017), 12:e786-e806.

Seo et al., "Characterization of bioactive RGD peptide immobilized onto poly(acrylic acid) thin films by plasma polymerization," Applied Surface Science, 2010, 257:596-602.

Stratesteffen et al., "GelMA-collagen blends enable drop-on-demand 3D printability and promote angiogenesis," Biofabrication, 2017, 9:045002, 1-12.

Vila et al., "Hydrogel co-networks of gelatine methacrylate and poly(ethylene glycol) diacrylate sustain 3D functional in vitro models of intestinal mucosa," Biofabrication, 2020, 12:025008, 1-16.

Wang et al., "Development of a Photo-Crosslinking, Biodegradable GelMA/PEGDA Hydrogel for Guided Bone Regeneration Materials," Materials, Aug. 3, 2018, 11:1345, 1-12.

Yin et al., "3D Bioprinting of Low-Concentration Cell-Laden Gelatin Methacrylate (GelMA) Bioinks with a Two-Step Crosslinking Strategy," ACS Applied Materials & Interfaces, Feb. 6, 2018, 10:6849-6857.

Yue et al., "Synthesis, properties, and biomedical applications of gelatin methacryloyl (GelMA) hydrogels," Biomaterials, 2015, 73:254-271.

Zhuang et al., "Layer-by-layer ultraviolet assisted extrusion-based (UAE) bioprinting of hydrogel constructs with high aspect ratio for soft tissue engineering applications," PLoS One, 2019, 14(6):e0216776, 1-21.

U.S. Appl. No. 17/738,686, filed May 6, 2022, Melican et al.

U.S. Appl. No. 17/738,694, filed May 6, 2022, Kaur et al.

U.S. Appl. No. 17/738,698, filed May 6, 2022, King et al.

U.S. Appl. No. 17/738,736, filed May 6, 2022, Melican et al.

U.S. Appl. No. 17/738,833, filed May 6, 2022, Modaresifar et al.

Akentjew et al., "Rapid fabrication of reinforced and cell-laden vascular grafts structurally inspired by human coronary arteries," Nature Communications, Dec. 1, 2019, 10(1):1-15.

Ali et al., "A Photo-Crosslinkable Kidney ECM-Derived Bioink Accelerates Renal Tissue Formation," Advanced Healthcare Materials, Apr. 1, 2019, 8(7):e1800992, 10 pages.

Baek et al., "In situ assembly of the collagen-polyacrylamide interpenetrating network hydrogel: Enabling decoupled control of stiffness and degree of swelling, " European Polymer Journal, Nov. 1, 2015, 72:413-422.

Bilisik et al., "3D fabrics for technical textile applications," in Non-woven Fabrics, Chapter 4, Intech, 2016, 81-141.

Calo et al., "Biomedical applications of hydrogels: A review of patents and commercial products," European Polymer Journal, Apr. 2015, 65:252-267.

Fukao et al., "Hydrogels toughened by biominerals providing energy-dissipative sacrificial bonds," J. Mater. Chem. B, 2020, 8:5184-5188.

Galliger et al., "3D bioprinting for lungs and hollow organs," Translational Research, May 14, 2019, 211:19-34.

Han, Hai-Chao, "Twisted Blood Vessels: Symptoms, Etiology and Biomechanical Mechanisms," J. Vasc. Res., May 2012 (online Mar. 14, 2012), 49(3):185-197.

Koobatian et al., "Surgical Technique for the Implantation of Tissue Engineered Vascular Grafts and Subsequent In Vivo Monitoring," J. Vis. Exp., Apr. 3, 2015, (98):52354, 1-11.

Marga et al., "Toward engineering functional organ modules by additive manufacturing," Biofabrication, Jun. 1, 2012, 4(2):022001, 13 pages.

Pashneh-Tala et al., "The Tissue-Engineered Vascular Graft-Past, Present and Future," Tissue Engineering: Part B, 2016 (online Oct. 7, 2015), 22(1):68-100.

Weigel et al., "Photopolymer formulations for uSL printing of hydrogel microstructures as swellable functional elements," Progress in Biomedical Optics and Imaging, SPIR—International Society for Optical Engineering, Mar. 5, 2021, 11637:116370A-1-116370A13.

Zhu et al., "Bioactive modification of poly(ethylene glycol) hydrogels for tissue engineering," Biomaterials, Jun. 1, 2010, 31(17):4639-4656.

Ha et al., "Conductive GelMA-Collagen-AgNW Blended Hydrogel for Smart Actuator," Polymers, Apr. 9, 2021, 13:1217, 1-10.

Kinstlinger et al., "Generation of model tissues with dendritic vascular networks via sacrificial laser-sintered carbohydrate templates," Nature Biomedical Engineering, Jun. 29, 2020, 4(9):916-932. doi: 10.1038/s41551-020-0566-1.

Vo et al., "Solvent Choice during Flow Assembly of Photocross-Linked Single-Chain Nanoparticles and Micelles Affects Cellular Uptake," ACS Appl. Mater. Interfaces, Nov. 6, 2024, 16(44):59833-59848.

* cited by examiner (a)

(b)

CONTROLLING THE SIZE OF 3D PRINTING HYDROGEL OBJECTS USING HYDROPHILIC MONOMERS HYDROPHOBIC MONOMERS, AND CROSSLINKERS

CROSS-REFERENCE TO RELATED APPLICATIONS

This application claims priority to U.S. Provisional Application No. 63/185,300, filed May 6, 2021, the entire contents of which are incorporated herein by reference.

SUMMARY

Embodiments of this disclosure relate to a printable composition comprising: about 1 weight percent (wt %) to about 40 wt % of one or more hydrophilic monomers; a swelling control agent selected from a hydrophobic monomer, a short chain crosslinker, or a combination thereof; about 0.01 wt % to about 2 wt % of a photo initiator; and 0 wt % to about 75 wt % of a vehicle comprising a protic solvent, by weight of the printable composition; provided that when the swelling control agent is a hydrophobic monomer then the printable composition has a weight ratio of the hydrophilic monomer to the hydrophobic monomer of about 20:1 to about 1:20; and when the swelling control agent is a short chain crosslinker then the printable composition comprises about 0.01 wt % to about 5 wt % of the short chain crosslinker. In some embodiments, the hydrophilic monomer comprises one or more of hydroxy $C_{1-2}$ alkyl (meth)acrylates, poly(alkylene oxide) alkyl ether (meth)acrylates, N-hydroxy $C_{1-2}$ alkyl (meth)acrylamides, or mixtures thereof. In some embodiments, the hydrophilic monomer comprises one or more of poly(ethylene glycol) methyl ether acrylate (PEGMEA), poly(ethylene glycol) methyl ether methacrylate, poly(propylene glycol) methyl ether acrylate, poly(propylene glycol) methyl ether methacrylate, hydroxyethyl acrylate (HEA), N-hydroxyethyl acrylamide (HEAA), or mixtures thereof. In some embodiments, the one or more hydrophilic monomers are selected from the group consisting of PEGMA, HEA, or mixtures thereof. In some embodiments, the printable composition comprises about 5 wt % to about 35 wt % of the one or more hydrophilic monomers. In some embodiments, the printable composition comprises from about 5 wt % to about 25 wt % of the one or more hydrophilic monomers. In some embodiments, the hydrophobic monomer comprises one or more of hydroxyl $C_{3-6}$ alkyl (meth)acrylates, or mixtures thereof. In some embodiments, the hydrophobic monomer comprises one or more of hydroxyethyl methacrylate, hydroxypropyl acrylate (HPA 3-Hydroxypropyl acrylate and/or 2-Hydroxypropyl acrylate), hydroxypropylmethacrylate, hydroxybutyl acrylate (HBA), hydroxybutyl methacrylate, or mixtures thereof. In some embodiments, the weight ratio of hydrophilic monomers to hydrophobic monomers is about 15:1 to about 1:15. In some embodiments, the weight ratio of hydrophilic monomers to hydrophobic monomers is about 10:1 to about 1:10. In some embodiments, the weight ratio of hydrophilic monomers to hydrophobic monomers is about 5:1 to about 1:5. In some embodiments, the weight ratio of the hydrophilic monomers to the hydrophobic monomers is about 1:1 to about 1:3. In some embodiments, the printable composition comprises HPA and HEA present in a weight ratio of about 3:1 to about 1:3. In some embodiments, the printable composition comprises HBA and HEA present in a weight ratio of about 3:1 to about 1:3. In some embodiments, the short chain crosslinkers comprise poly(alkylene oxide) di(meth)acrylates having a weight average molecular weight ($M_w$) of about 400 to about 20,000, diethylene glycol di(meth)acrylate, tetraethylene glycol di(meth)acrylate, N,N'-methylenebis(acylamide), (poly)lactic acid di(meth)acrylate, (poly)glycolic acid di(meth)acrylate, (poly)lactic-coglycolide di(meth)acrylate, (poly)caprolactone di(meth)acrylate, (poly)dioxanone di(meth)acrylate, (poly)fumarate di(meth)acrylate, (caboxy)(methyl)cellulose di(meth)acrylate, hyaluronic acid di(meth)acrylate, heparan sulphate di(meth)acrylate, dextran di(meth)acrylate, alginate di(meth)acrylate, pectin di(meth)acrylate, or collagen di(meth)acrylate or mixtures thereof. In some embodiments, the poly(alkylene oxide) di(meth)acrylate comprises poly(ethylene glycol) diacrylate. In some embodiments, the printable composition comprises about 0.5 wt % to about 3 wt % of the short chain crosslinkers. In some embodiments, the photo initiator comprises lithium phenyl-2,4,6-trimethylbenzoylphosphinate (LAP), Trimethylbenzoyl based photoinitiators, diphenyl(2,4,6-trimethylbenzoyl)phosphine oxide (TPO nanoparticle) Irgacure class of photoinitiators, ruthenium, and riboflavin, or mixtures thereof. In some embodiments, the printable composition further comprises one or more additives comprising polymers, UV dyes, natural extracellular matrices, photoinitiators, Peptides, amino acids, growth factors, denature extracellular matrices, extracellular matrix fragments or mixtures thereof. In some embodiments, the protic solvent comprises water, polyethylene glycol, Glycol diacrylate derivatives or mixtures thereof.

Additional embodiments include a method of preparing a three-dimensional article comprising printing a printable composition according to any one of the embodiments to fabricate the three-dimensional article. In some embodiments, the printing fabricates a three-dimensional article of an organ, wherein the organ is a mammalian organ. In some embodiments, the printing comprises ink jet printing, extrusion printing, or layer-by-layer printing. In some embodiments, the three-dimensional article has a swelling percentage of less than about 300% by weight, based on the non-hydrated weight of the three-dimensional article. In some embodiments, the three-dimensional article has a swelling percentage of about 1% to less than about 300% by weight, based on the non-hydrated weight of the three-dimensional article. Additional embodiments include a three-dimensional article manufactured according to the method of these embodiments.

Additional embodiments include a method of manufacturing a three-dimensional article comprising: depositing a layer of a printable composition to a surface to obtain a deposited layer; irradiating the deposited layer; and repeating the depositing and irradiating steps until the deposited layers form the three-dimensional article, wherein the printable composition comprises: about 1 weight percent (wt %) to about 40 wt % of one or more hydrophilic monomers; a swelling control agent selected from a hydrophobic monomer, a short chain crosslinker, or a combination thereof; about 0.01 wt % to about 2 wt % of a photo initiator; and 0 wt % to about 75 wt % of a vehicle comprising a protic solvent, by weight of the printable composition; provided that when the swelling control agent is a hydrophobic monomer then the printable composition has a weight ratio of the hydrophilic monomer to the hydrophobic monomer of about 20:1 to about 1:20; and when the swelling control agent is a short chain crosslinker then the printable composition comprises about 0.01 wt % to about 5 wt % of the short chain crosslinkers. In some embodiments, the printable composition is a printable composition according to any one of the embodiments. In some embodiments, the deposited layer is irradiated at a wavelength from about 365 nm to about 405 nm.

DETAILED DESCRIPTION

Figure 1:
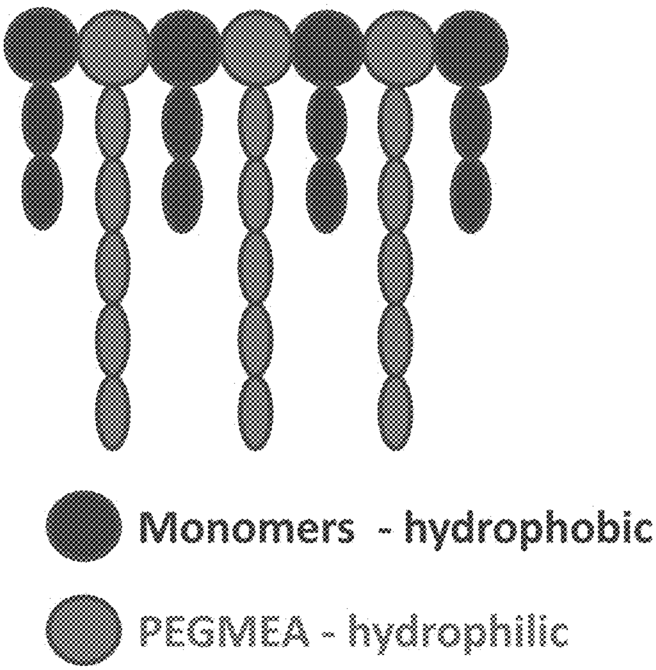
FIG. 1 shows an embodiment of an HPA-PEGMEA brush copolymer.

The present disclosure includes printable composition comprising: hydrophilic monomer(s), hydrophobic monomer(s), a short chain crosslinker(s), a photo initiator, solvent and/or a combination thereof. These compositions may be hydrogels. By manipulating the content of the hydrogel, such as varying amounts of hydrophilic and/or hydrophobic monomer, the shape of the resulting hydrogel when exposed to an aqueous environment, including a physiological environment, can be controlled. The disclosure also includes methods of preparing a three-dimensional article comprising printing a printable composition, and three-dimensional articles manufactured according to these methods.

As used herein, the singular forms “a,” “an,” and “the” include plural referents unless the content clearly dictates otherwise. For example, reference to “a cell” includes a combination of two or more cells, and the like.

As used herein, “weight percent” (also expressed as “wt %”), refers to the percent of one or more components relative to the total mass of the composition. Thus, a composition with a mass of 100 grams comprising 10 grams of Compound A has a weight percent of 10% for Compound A. As used herein, weight percent is used synonymously with mass percent.

As used herein, the terms “object” and “article” may be used interchangeably and refer to items comprising the compositions of the invention.

As used herein, the term “comprising” or “comprises” is intended to mean that the compositions and methods include the recited elements, but not excluding others. “Consisting essentially of” when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. “Consisting of” shall mean excluding more than trace elements of other ingredients and substantial method steps. Embodiments defined by each of these transition terms are within the scope of this invention. When an embodiment is defined by one of these terms (e.g., “comprising”) it should be understood that this disclosure also includes alternative embodiments. Some of these embodiments may include “consisting essentially of” and “consisting of” for said embodiment.

As used herein, “swelling percent” or “percent swelling” means, unless otherwise specified, the percent change in mass of an object before and after incubation in water. Thus, a positive percentage indicates that the object has increased in size and a negative percentage indicates the object has decreased in size.

As used herein, the terms “substantially” and “about” are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. When referring to a first numerical value as “substantially” or “about” the same as a second numerical value, the terms can refer to the first numerical value being within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In some embodiments, the percent change is over a time period of the incubation in water of the object or article. In some embodiments, the time period is selected from about 5 s to about 30 s, about 30 s to about 1 min, about 1 min to about 10 min, about 10 min to about 30 min, about 30 min to about 1 hr, about 1 hr to about 3 hr, about 3 hr to about 12 hr, about 12 hr to about 24 hr, about 24 hr to about 1 week (w), about 1 w to about 4 w, about 1 month to about 6 months, about greater than 6 months, or any range between any two of the values.

In some embodiments, the object, article or composition, achieves a steady state of mass over a time period is selected from about 5 s to about 30 s, about 30 s to about 1 min, about 1 min to about 10 min, about 10 min to about 30 min, about 30 min to about 1 hr, about 1 hr to about 3 hr, about 3 hr to about 12 hr, about 12 hr to about 24 hr, about 24 hr to about 1 week (w), about 1 w to about 4 w, about 1 month to about 6 months, about greater than 6 months, or any range between any two of the values.

A "steady state of mass," as used herein, comprises a state where the mass of the composition or article remains constant even upon remaining incubated in water.

The present application incorporates by reference in their entirety each of the following documents: (a) U.S. provisional application No. 63/185,293 filed May 6, 2021 titled "USE OF FUNCTIONALIZED AND NON-FUNCTIONALIZED ECMS, ECM FRAGMENTS, PEPTIDES AND BIOACTIVE COMPONENTS TO CREATE CELL ADHESIVE 3D PRINTED OBJECTS" and U.S. non-provisional and/or PCT application(s) under the same title filed on May 6, 2022; (b) U.S. provisional application No. 63/185,302 filed May 6, 2021 titled "MODIFIED 3D-PRINTED OBJECTS AND THEIR USES" and U.S. non-provisional and/or PCT application(s) under the same title filed on May 6, 2022; (c) U.S. provisional application No. 63/185,305 filed May 6, 2021 titled "PHOTOCURABLE REINFORCEMENT OF 3D PRINTED HYDROGEL OBJECTS" and U.S. non-provisional and/or PCT application(s) under the same title filed on May 6, 2022; (d) U.S. provisional application No. 63/185,299 filed May 6, 2021 titled "ADDITIVE MANUFACTURING OF HYDROGEL TUBES FOR BIOMEDICAL APPLICATIONS" and U.S. non-provisional and/or PCT application(s) under the same title filed on May 6, 2022; (e) U.S. provisional application No. 63/185,298 filed May 6, 2021 titled "MICROPHYSIOLOGICAL 3-D PRINTING AND ITS APPLICATIONS" and U.S. non-provisional and/or PCT application(s) under the same title filed on May 6, 2022.

Compositions

Certain embodiments of the present disclosure relate to compositions comprising: hydrophilic monomer(s) and/or polymers, hydrophobic monomer(s) and/or polymers, a short chain crosslinker(s), a photo initiator, solvent and/or a combination thereof. In some embodiments, these compositions are printable, e.g., capable of being used in the 3-D printer.

Some embodiments include a printable composition comprising: about 1 weight percent (wt %) to about 40 wt % of one or more hydrophilic monomers; a swelling control agent selected from a hydrophobic monomer, a short chain crosslinker, or combinations thereof. The composition may comprise about 0.01 wt % to about 2 wt % of a photo initiator and/or 0 wt % to about 75 wt % of a vehicle comprising a protic solvent, by weight of the printable composition.

Hydrophilic monomers of the present disclosure are not particularly limited as long as they are suitable for the intended purposes. In some embodiments, the hydrophilic monomer comprises an acrylate or methacrylate moiety and a hydrophilic sidechain attached to the (meth)acrylate. In some embodiments, the hydrophilic monomer is water soluble, e.g., the monomer or a homopolymer is water soluble. Exemplary embodiments of the hydrophilic monomer include one or more of hydroxy $C_{1-2}$ alkyl (meth) acrylates, poly(alkylene oxide) alkyl ether (meth)acrylates, N-hydroxy $C_{1-2}$ alkyl (meth)acrylamides, and mixtures thereof. In additional embodiments of the hydrophilic monomer comprises one or more of poly(ethylene glycol) methyl ether acrylate (PEGMEA), poly(ethylene glycol) methyl ether methacrylate, poly(propylene glycol) methyl ether acrylate, poly(propylene glycol) methyl ether methacrylate, hydroxyethyl acrylate (HEA), N-hydroxyethyl acrylamide (HEAA), hydrophilic acrylate, hydrophilic vinyl, hydrophilic non-ionic, hydrophilic ionic, graft hydrophilic, hydrophobic acrylate, hydrophobic vinyl, hydrophobic non-ionic, hydrophobic ionic, graft hydrophobic, or mixtures thereof. In some embodiments, the composition may comprise peptides, cleavable peptide monomers, dithiol monomers, thiol-acrylates, diacrylates, and PEG-diacrylates. In particular embodiments, the one or more hydrophilic monomers are selected from the group consisting of PEGMA, HEA, or mixtures thereof. In particular embodiments, the one or more hydrophilic monomers include PEGMA and a second hydrophilic monomer. In some embodiments, the composition includes about 10, 15, 20, 25, or 30 wt % PEGMA and optionally a second hydrophilic monomer. In some embodiments, the second hydrophilic monomer is less hydrophilic and/or has a shorter side chain than the PEGMA. In some embodiments, the PEGMA includes the following monomer:

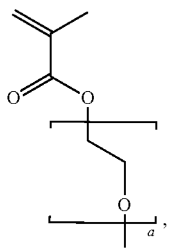

where a is an integer of 2-20 (e.g., 2, 3, 4, 8, 20, etc.). The integer a can be a mixture of a single value, for example:

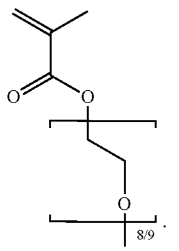

FIG. 1 shows an embodiment of a HPA-PEGMEA brush copolymer.

In some embodiments, when the swelling control agent is a hydrophobic monomer then the printable composition has a weight ratio of the hydrophilic monomer to the hydrophobic monomer of about 100:1 to about 1:100. For example, certain embodiments include a weight ratio of the hydrophilic monomer to the hydrophobic monomer of about 100:1, about 90:1, about 80:1, about 70:1, about 60:1, about 50:1, about 40:1, about 30:1, about 20:1, about 10:1, about 1:1, about 1:10, about 1:20, about 1:30, about 1:40, about 1:50, about 1:60, about 1:70, about 1:80, about 1:90, or about 1:100, or any range between any two of the values. For example, in some embodiments, the weight ratio of the hydrophilic monomer to the hydrophobic monomer is about 20:1 to about 1:20, about 15:1 to about 1:15, about 10:1 to about 1:10, about 5:1 to about 1:5, about 3:1 to about 1:3, about 1:1 to about 1:3. These weight ratios of the hydrophilic monomer (or polymer) to the hydrophobic monomer (or polymer) include, e.g., HPA and HEA (or PEGMA) or HBA and HEA (or PEGMA). In some embodiments, hydrophobic and hydrophilic monomers can be used in place of or in addition to the monomers in the same ratios disclosed for the monomers. When polymers are used in combination with monomers, the ratios disclosed are the sum of hydrophobic and hydrophilic respectively (hydrophilic monomers+hydrophilic polymers:hydrophobic monomers+hydrophobic polymers).

Hydrophobic monomers of the present disclosure are not particularly limited as long as they are suitable for the intended purposes. In some embodiments, the hydrophobic monomer comprises an acrylate or methacrylate moiety and a hydrophobic sidechain attached to the (meth)acrylate. In some embodiments, the hydrophobic monomer is not water soluble, e.g., the monomer or a homopolymer is not water soluble. In some embodiments, the hydrophobic monomer is hydrophobic relative to the other monomers in the composition. Non-limiting examples of hydrophobic monomers include one or more of hydroxyl $C_{3-10}$ alkyl (meth)acrylates, or mixtures thereof (e.g., hydroxyethyl methacrylate, hydroxypropyl acrylate (HPA), hydroxypropylmethacrylate, hydroxybutyl acrylate (HBA), hydroxybutyl methacrylate, hydrophilic acrylate, hydrophilic vinyl, hydrophilic non-ionic, hydrophilic ionic, graft hydrophilic, hydrophobic acrylate, hydrophobic vinyl, hydrophobic non-ionic, hydrophobic ionic, graft hydrophobic, or mixtures thereof). In some embodiments, the $C_{3-10}$ alkyl (meth)acrylate is a $C_3$, $C_4$, $C_5$, $C_6$, $C_7$, $C_8$, $C_9$, $C_{10}$ alkyl (meth)acrylate. In some embodiments, the alkyl (meth)acrylate is optionally substituted, e.g., with a hydrophobic moiety, such as an aryl group or a hydrocarbon group. In some embodiments, the composition comprises peptide monomers, cleaveable peptide monomers, dithiol monomers, thiol-acrylates, diacrylates, PEG-diacrylates, and combinations thereof.

In some embodiments, when the swelling control agent is a short chain crosslinker then the printable composition comprises about 0.01 wt % to about 10 wt % of the short chain crosslinker. Exemplary embodiments include where the printable composition comprises about 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, 7, 7.5, 8, 8.5, 9, 9.5, or 10 wt % of the short chain crosslinker, or any range between any two of the values. For example, in some embodiments, the printable composition comprises about 0.01 wt % to about 5 wt % of the short chain crosslinker.

The short chain crosslinkers include, e.g., poly(alkylene oxide) di(meth)acrylates having a weight average molecular weight ($M_w$) of about 400 to about 20,000, diethylene glycol di(meth)acrylate, tetraethylene glycol di(meth)acrylate, N,N'-methylenebis(acylamide), (poly)lactic acid di(meth) acrylate, (poly)glycolic acid di(meth)acrylate, (poly)lactic-coglycolide di(meth)acrylate, (poly)caprolactone di(meth) acrylate, (poly)dioxanone di(meth)acrylate, (poly)fumarate di(meth)acrylate, (caboxy)(methyl)cellulose di(meth)acrylate, hyaluronic acid di(meth)acrylate, heparan sulphate di(meth)acrylate, dextran di(meth)acrylate, alginate di(meth)acrylate, pectin di(meth)acrylate, or collagen di(meth) acrylate or mixtures thereof. In some embodiments, the poly(alkylene oxide) di(meth)acrylate comprises poly(ethylene glycol) diacrylate The photo initiator is not particularly limited. In some embodiments, it is such as to allow for onset times from 0-60 seconds. In some embodiments, the photo initiator comprises lithium phenyl-2,4,6-trimethylbenzoylphosphinate (LAP), trimethylbenzoyl based photoinitiators, diphenyl(2,4,6-trimethylbenzoyl)phosphine oxide (TPO nanoparticle) Irgacure® class of photoinitiators, ruthenium, and riboflavin, or mixtures thereof.

The printable composition can further comprise one or more additives comprising polymers, UV dyes, natural extracellular matrices, peptides, amino acids, growth factors, denature extracellular matrices, extracellular matrix fragments or mixtures thereof.

The solvent is not particularly limited as long as it allows for 3-D printing and/or allows for polymerization. In some embodiments, the solvent is a protic solvent, e.g., a protic solvent that comprises water, polyethylene glycol, glycol diacrylate derivatives or mixtures thereof.

In some embodiments, the printable composition permits onset times from greater than 0 to about 60 seconds (e.g., about 1, 2, 3, 4, 5, 10, 15, 20, 30, 40, 50, 60 seconds). In some embodiments, the printable composition permits resolution down to 100, 50, 25, 25, 1 micron or less in a 3-D printer. In some embodiments, the printable composition results in a printed composition having a green strength ranging from about 10 kPa to about 1 MPa.

Methods

Certain embodiments of the present disclosure relate to preparing a three-dimensional article comprising printing a printable composition according to the embodiments herein. In some embodiments, the printing fabricates a three-dimensional organ or components of an organ. For example the three-dimensional object can be a mammalian organ, e.g., a lung, or a components of a mammalian organ, e.g., bronchioles. In some embodiments, the printing comprises ink jet printing, extrusion printing, or layer-by-layer printing. In some embodiments, the methods further include irradiating the printed composition. In some embodiments, the composition is irradiated at a wavelength from about 365 nm to about 405 nm.

Certain embodiments of the present disclosure relate to a method of manufacturing a three-dimensional article comprising: depositing a layer of a printable composition to a surface to obtain a deposited layer; irradiating the deposited layer; and repeating the depositing and irradiating steps until the deposited layers form the three-dimensional article, wherein the printable composition is a composition disclosed herein. In some embodiments, the deposited layer is irradiated at a wavelength from about 365 nm to about 405 nm.

In some embodiments the printable composition comprises: about 1 weight percent (wt %) to about 40 wt % of one or more hydrophilic monomers; a swelling control agent selected from a hydrophobic monomer, a short chain crosslinker, or a combination thereof; about 0.01 wt % to about 2 wt % of a photo initiator; and 0 wt % to about 75 wt % of a vehicle comprising a protic solvent, by weight of the printable composition; provided that when the swelling control agent is a hydrophobic monomer then the printable composition has a weight ratio of the hydrophilic monomer to the hydrophobic monomer of about 20:1 to about 1:20; and when the swelling control agent is a short chain crosslinker then the printable composition comprises about 0.01 wt % to about 5 wt % of the short chain crosslinkers.

In some embodiments, the three-dimensional article has a swelling percentage of less than about 300% by weight, based on the non-hydrated weight of the three-dimensional article. In some embodiments, the swelling percentage is less than about 300%, 250%, 200, 175%, 150% by weight, based on the non-hydrated weight of the three-dimensional article. In some embodiments, the swelling percentage is at least about 1%, 2%, 3%, 4%, 5%, 10%, 20%, 50%, 60%, 70%, 80%, 90%, or 100%, based on the non-hydrated weight of the three-dimensional article. The three-dimensional article may also have a swelling percentage within a range of the above values, for example, in some embodiments, the three-dimensional article has a swelling percentage of about 1% to less than about 300% by weight, based on the non-hydrated weight of the three-dimensional article.

In some embodiments, the methods further include one or more step of surface modification, post processing to promote cell attachment, addition of cells, mechanical stimulation: expansion, contraction, and/or perfusion.

The present disclosure also includes embodiments of a three-dimensional article manufactured according to the methods of this disclosure.

EXAMPLES

The following example describes specific aspects of some embodiments of this disclosure to illustrate and provide a description for those of ordinary skill in the art. The example should not be construed as limiting this disclosure, as the example merely provides specific methodology useful in understanding and practicing some embodiments of this disclosure.

30-45% PEGMEA Hydrogel and 25-35% PEGMEA Hydrogel

Hydrogels were formed by initiating polymerization of the following compositions:

| 30-45% PEGMEA Mn = 480 | | 25-35% PEGMEA Mn = 480 | |
|---|---|---|---|
| Reagents | Wt (%) | Reagents | Wt (%) |
| 36.7 wt/vol % PEGDA 10k | 1-10 | 55 wt./vol % PEGDA 3.4k | 1-10 |
| PEGMEA 480 | 30-45 | PEGMEA 480 | 25-35 |
| 2-5 wt/vol % LAP | 15-30 | 2-5 wt/vol % LAP | 15-30 |
| 1-5 wt/vol % UV | 2.67 | 1-5 wt/vol % UV | 2.67 |
| Solvent | remainder | Solvent | remainder |
| | 100 | | 100 |

Figure 2A:
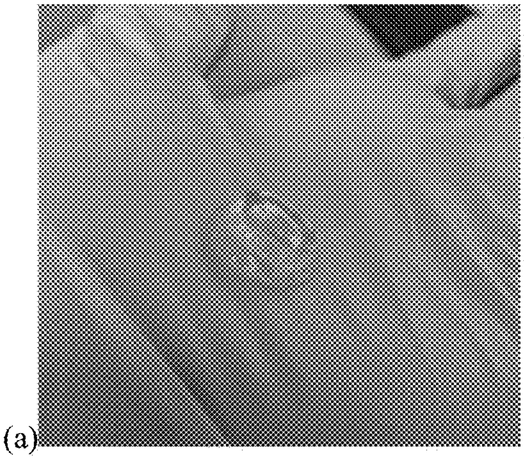
FIG. 2A shows the swelling of a particular 30-45% PEGMEA hydrogel.
Figure 2B:
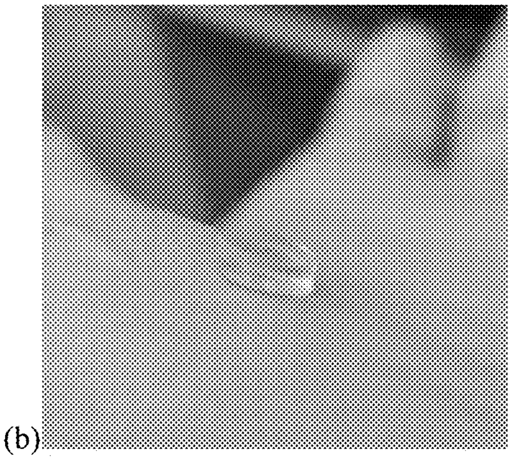
FIG. 2B shows the swelling of a particular 25-35% PEGMEA hydrogel.

Both compositions were weighed before and after being placed in an aqueous buffer overnight. As shown in FIG. 2(*a*), 30-45% PEGMEA hydrogel swelled uncontrollably and did not retain shape once placed in buffer. It showed a >300% increase in weight. As shown in FIG. 2(*b*), dropping PEGMEA content from 30-45% to 25-35% and introducing 1% PEGDA3.4 k significantly improved retention of sample shape.

Controlling Swelling with a Monomer (2-Hydroxypropyl Acrylate)

Additional hydrogels were synthesized based on the 25-35% PEGMEA hydrogel, where specific amounts of PEGMEA was replaced with hydrophobic 2-Hydroxypropyl acrylate (2-HPA).

| 1:1 PEGMEA/HPA | | 2:1 PEGMEA/HPA | |
|---|---|---|---|
| Reagents | Wt (%) | Reagents | Wt (%) |
| HPA | 10-18 | HPA | 5-9 |
| PEGMEA | 10-18 | PEGMEA | 10-18 |
| 55 wt/vol % PEGDA 3.4k | 1-10 | 55 wt/vol % PEGDA 3.4k | 1-10 |
| $DIH_2O$ | 40-50 | $DIH_2O$ | 45-55 |
| 4 wt/vol % LAP | 20-30 | 4 wt/vol % LAP | 20-30 |
| 3 wt/vol % UV | 2.67 | 3 wt/vol % UV | 2.67 |
| | 100 | | 100 |

| 25-35% HPA | | 25-35% PEGMEA | |
|---|---|---|---|
| Reagents | Wt (%) | Reagents | Wt (%) |
| HPA | 25-35 | 55 wt/vol % PEGDA 3.4k | 1-10 |
| 55 wt/vol % PEGDA 3.4k | 1-10 | PEGMEA | 25-35 |
| $DIH_2O$ | 40-50 | $DIH_2O$ | 40-50 |
| 4 wt/vol % LAP | 20-30 | 4 wt/vol % LAP | 20-30 |
| 3 wt/vol % UV | 2.67 | 3 wt/vol % UV | 2.67 |
| | 100 | | 100 |

Figure 3:
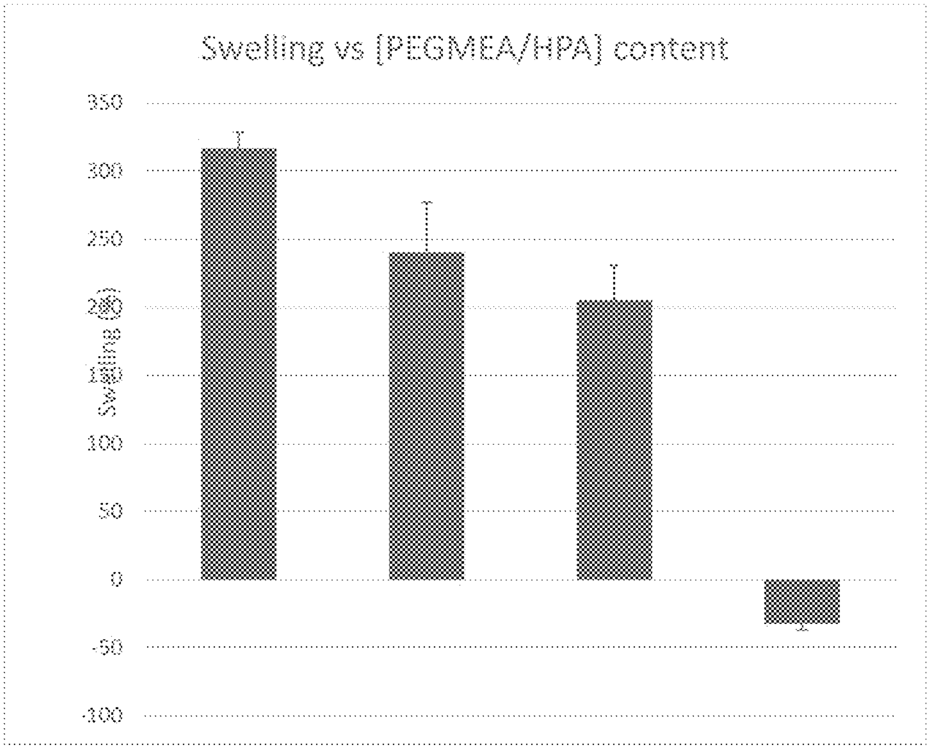
FIG. 3 shows swelling values for specific embodiments having different weight percent ratios of hydropholic monomer poly(ethylene glycol) methyl ether acrylate (PEGMEA) and hydrophobic monomer 2-hydroxypropyl acrylate (HPA) (1:0, 2:1, 1:1, 1:0).

As shown in FIG. 3, the swelling values were respectively:

25-35 PEGMEA=316.7%

2:1 PEGMEA/HPA=240.1%

1:1 PEGMEA/HPA=205.3%

25-35 HPA=−32.4%.

Figure 4:
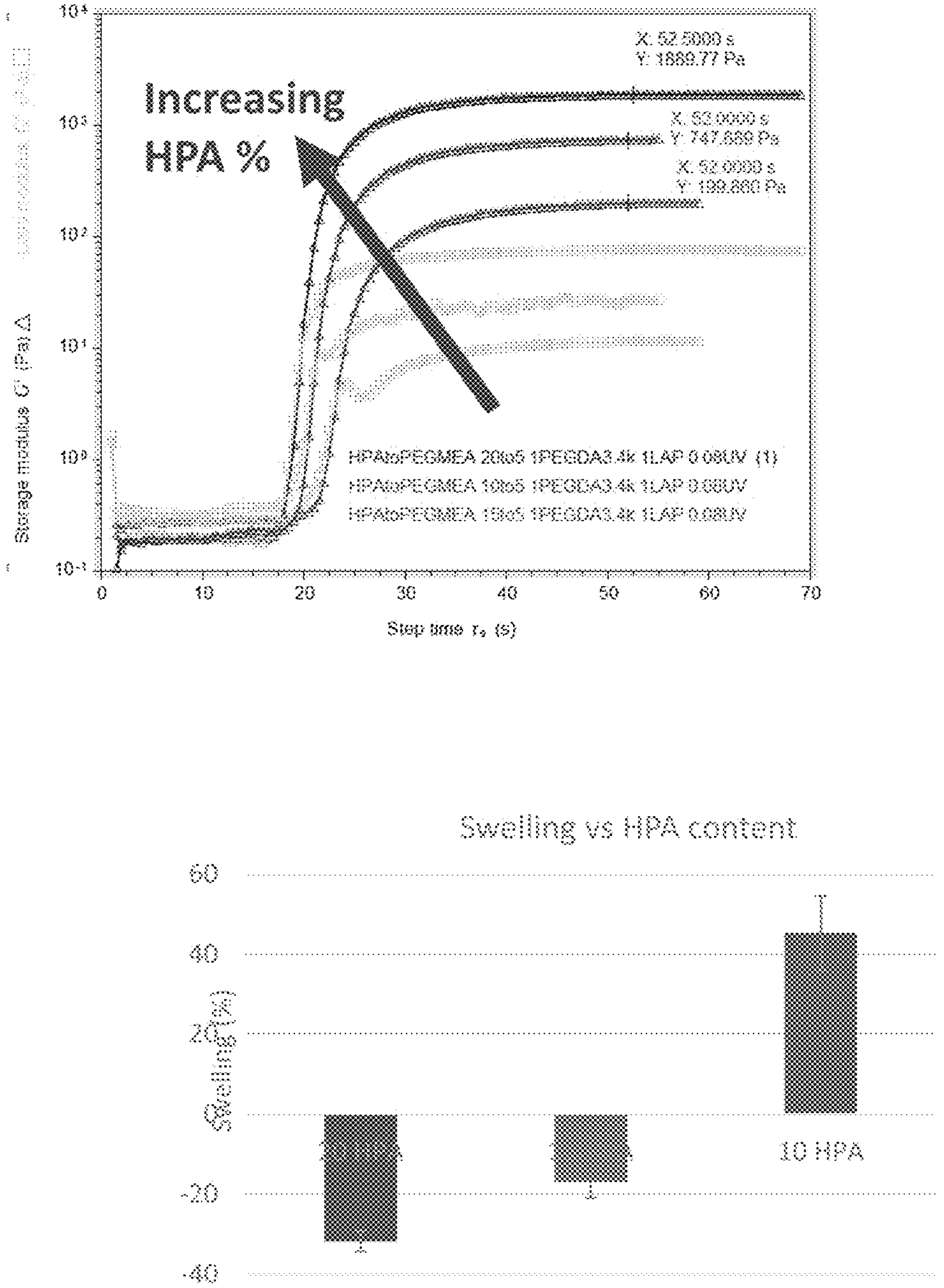
FIG. 4 shows swelling data for additional embodiments having varying HPA:PEGMEA weight percent ratios.

As shown in FIG. 4, other HPA:PEGMEA ratios were explored to modulate swelling including 4:1, 2:1, 3:1.

| 4:1 HPA:PEGMEA | | 3:1 HPA:PEGMEA | |
|---|---|---|---|
| Reagents | Wt (%) | | Wt (%) |
| HPA | 16-24 | Extra $DIH_2O$ | 1-10 |
| PEGMEA | 4-6 | HPA | 9-18 |
| 55 wt/vol % PEGDA 3.4k | 1-2 | PEGMEA | 3-6 |
| DI H2O | remainder | 55 wt/vol % PEGDA 3.4k | 1-2 |
| 5 wt/vol % LAP | 15-30 | $DIH_2O$ | remainder |
| 3 wt/vol % UV | 2.67 | 5 wt/vol % LAP | 15-25 |
| | 100 | 3 wt/vol % UV | 2.67 |
| | | | 100 |

| 2:1 HPA:PEGMEA | | |
|---|---|---|
| | Wt (%) | Wt (g) |
| Extra DIH2O | 10 | X |
| HPA | 8-18 | 1.5 |
| PEGMEA | 4-9 | X |
| 55 wt/vol % PEGDA 3.4k | 1-2 | X |
| $DIH_2O$ | 50-55 | X |
| 5 wt/vol % LAP | 15-25 | X |
| 3 wt/vol % UV | 2.67 | X |
| | 100 | X |

As shown in the following tables, varying brush polymer to monomer ratio allowed for effective modulation of swelling outcome. This control was also reproducible.

| 4:1 HPA | Wt (mg) | Wt (mg) | Wt (%) |
|---|---|---|---|
| 1 | X | X | −30.3226 |
| 2 | X | X | −32.6923 |
| 3 | X | X | −30.3226 |

-continued

| | | | |
|---|---|---|---|
| 4 | X | X | −36.3636 |
| 5 | X | X | −29.4118 |
| 6 | X | X | −31.3725 |
| avg | | | −31.7476 |
| stdev | | | 2.524219 |
| 3:1 HPA | Wt (mg) | Wt (mg) | Wt (%) |
| 1 | X | X | −21.4286 |
| 2 | X | X | −22.6891 |
| 3 | X | X | −13.9344 |
| 4 | X | X | −13.2813 |
| 5 | X | X | −15.2672 |
| 6 | X | X | −14.5161 |
| avg | | | −16.8528 |
| stdev | | | 4.1048 |
| 2:1 HPA | Wt (mg) | Wt (mg) | Wt (%) |
| 1 | X | X | 49.54955 |
| 2 | X | X | 35.2 |
| 3 | X | X | 61.76471 |
| 4 | X | X | 42.98246 |
| 5 | X | X | 41.12903 |
| 6 | X | X | 41.44144 |
| avg | | | 45.34453 |
| stdev | | | 9.260667 |

Controlling Swelling with Monomers (HEA C2, HPA C3, HBA C4)

Additional polymers were made with other monomers besides HPA, including HBA and HEA, thereby demonstrating that controlled swelling can be obtained with a broad range of monomers.

| 1-3 wt % HPA, HBA, or HEA | |
|---|---|
| Reagents | Wt (%) |
| 4-HBA, 2-HEA, or 2-HPA | 1-3 |
| PEGDA575 | 0.1-2 |
| PEGMEA | 8-15 |
| 55 wt/vol % PEGDA 3.4k | 2-5 |
| DIH20 | remainder |
| 4 wt/vol % LAP | 10-20 |
| 3 wt/vol % UV | 1.67 |
| | 102 |

Figure 5:
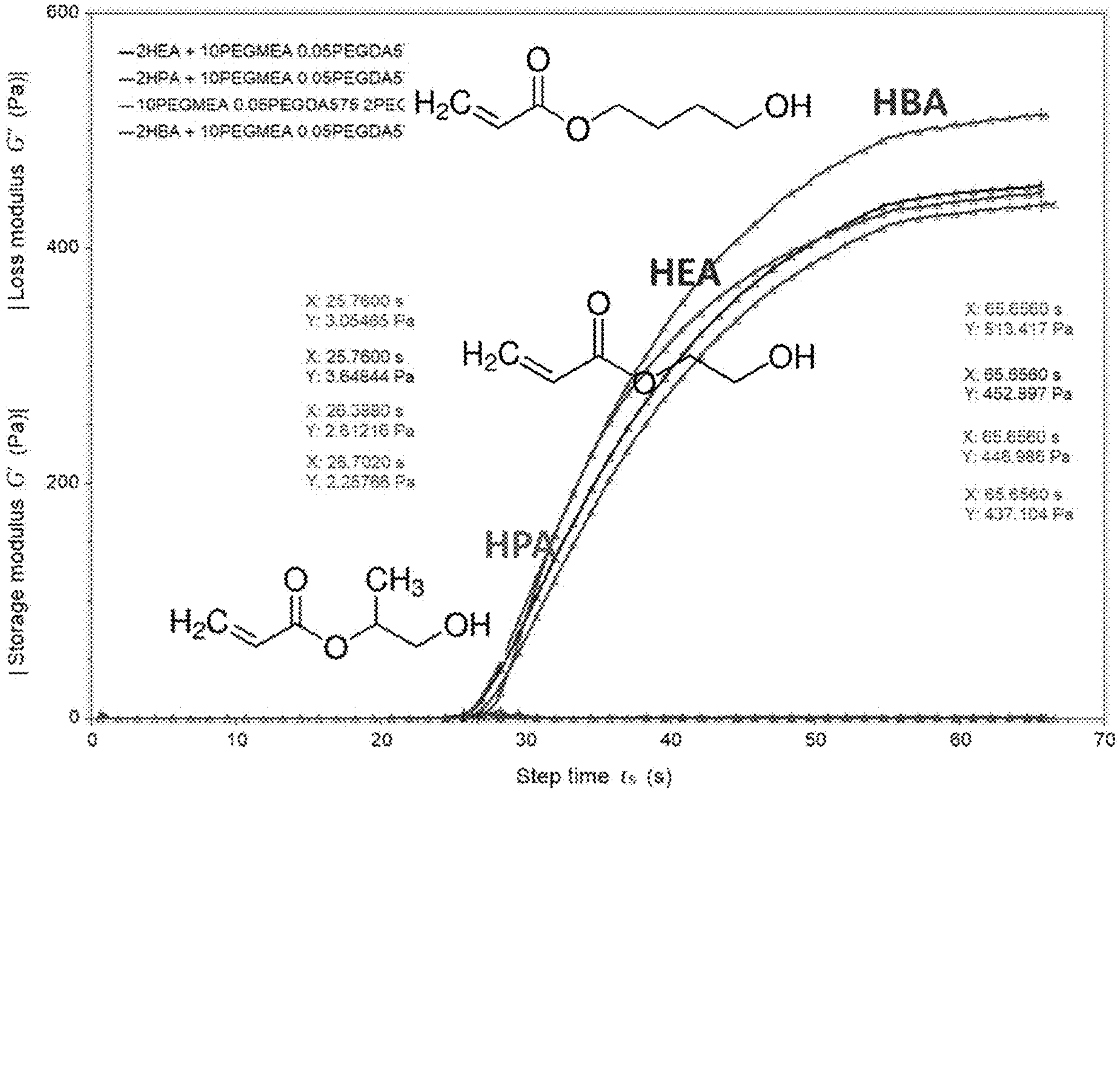
FIG. 5 shows specific embodiments of 10 PEGMEA with different monomers resulted in varied swelling.

FIG. 5 shows the 10 PEGMEA with monomers resulted in the following swelling values:

2HEA=96.21%

2HBA=79.86%

2HPA=75.89%.

Next, polymers with increasing [HPA/HEA] ratios and [HBA/HEA] ratios were synthesized using the following compositions:

| 3 HPA:2HEA | | 1 HPA:1 HEA | |
|---|---|---|---|
| Reagents | % Amount | Reagents | % Amount |
| HPA | 10-16 | HPA | 8-15 |
| HEA | 6-14 | HEA | 8-15 |
| PEGMEA | 5 | PEGMEA | 5 |
| 55 wt/vol % PEGDA3.4K | 1-3 | 55 wt/vol % PEGDA3.4K | 1-3 |
| DIH$_2$O | 3-7 | DIH$_2$O | 3-7 |
| 30 DOF 17.6 mg/ml | 40-56 | 30 DOF 17.6 mg/ml | 40-50 |
| 5 wt/vol % LAP | 15-20 | 5 wt/vol % LAP | 15-20 |

-continued

| 3 HPA:2HEA | | 1 HPA:1 HEA | |
|---|---|---|---|
| Reagents | % Amount | Reagents | % Amount |
| 5 wt/vol % LAP | 1-5 | 5 wt/vol % LAP | 1-5 |
| 3 wt/vol % Dye | 1-5 | 3 wt/vol % Dye | 1-5 |
| | 100 | | 100 |

| 2 HPA:3 HEA | |
|---|---|
| Reagents | % Amount |
| HPA | 10-16 |
| HEA | 6-14 |
| PEGMEA | 5 |
| 55 wt/vol % PEGDA3.4K | 1-3 |
| DIH$_2$O | 3-7 |
| 30 DOF 17.6 mg/ml | 40-50 |
| 5 wt/vol % LAP | 15-20 |
| 5 wt/vol % LAP | 1-5 |
| 3 wt/vol % Dye | 1-5 |
| | 100 |

| Reagents | Wt (%) |
|---|---|
| HPA | 3-8 |
| HEA | 12-20 |
| PEGMEA | 5 |
| 55 wt/vol % PEGDA3.4K | 1-3 |
| DIH$_2$O | 3-7 |
| 30 DOF 17.6 mg/ml | 40-50 |
| 5 wt/vol % LAP | 15-20 |
| 3 wt/vol % Dye | 1-5 |
| | 100 |

| Reagents | Wt (%) |
|---|---|
| HPA | 8-16 |
| HEA | 8-16 |
| PEGMEA | 5 |
| 55 wt/vol % PEGDA3.4K | v |
| DIH$_2$O | 5.11 |
| 30 DOF 17.6 mg/ml | 45.4 |
| 5 wt/vol % LAP | 20 |
| 3 wt/vol % Dye | 2.67 |
| | 100 |

| Reagents | Wt (%) |
|---|---|
| HPA | 10-15 |
| HEA | 10-15 |
| PEGMEA | 4-7 |
| 55 wt/vol % PEGDA3.4K | 1-3 |
| DIH$_2$O | 3-7 |
| 30 DOF 17.6 mg/ml | 40-50 |
| 5 wt/vol % LAP | 15-20 |
| 3 wt/vol % Dye | 1-5 |
| | 100 |

Figure 6:
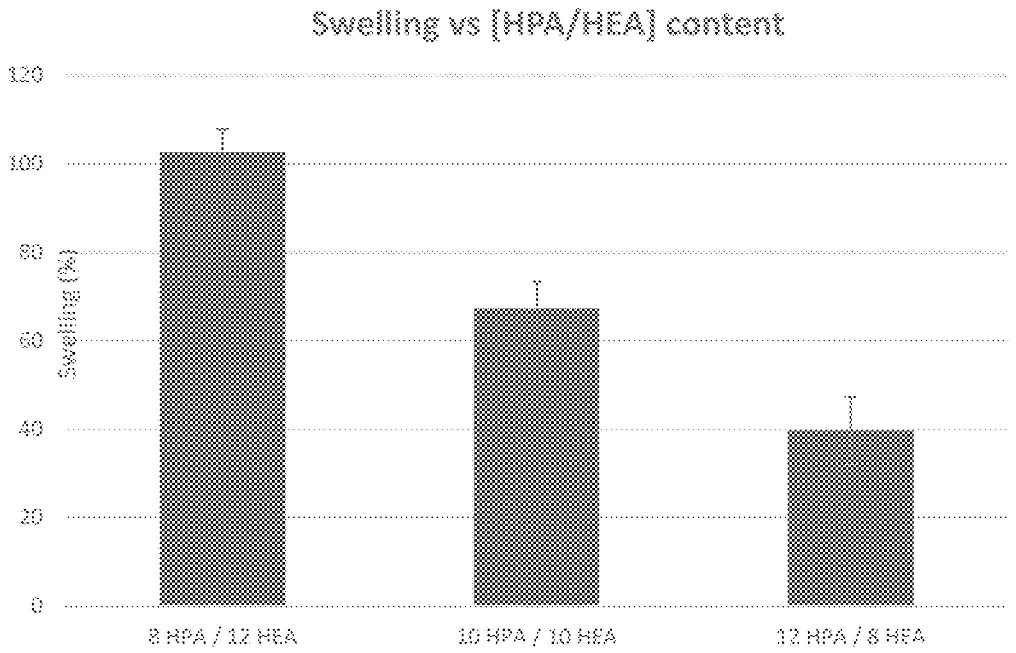
FIG. 6 shows the swelling versus [HPA/HEA] content in specific embodiments.
Figure 7:
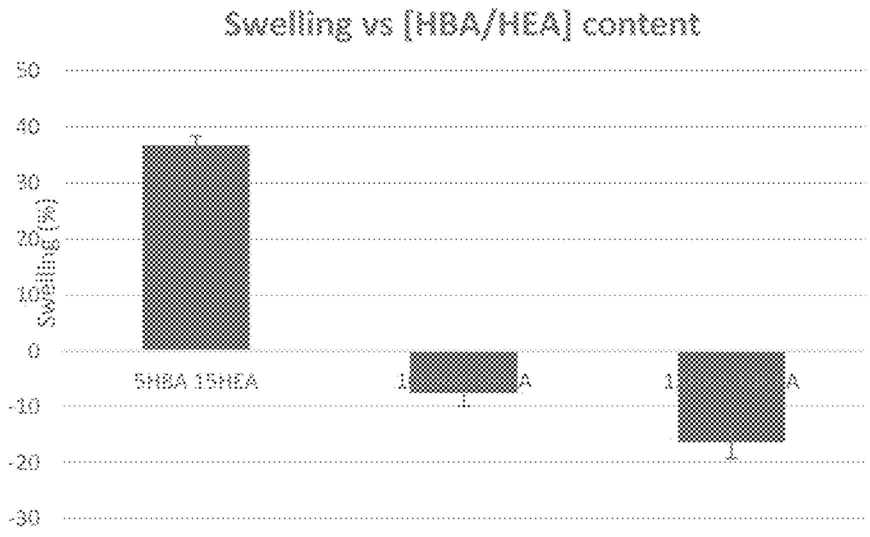
FIG. 7 shows the swelling versus [HBA/HEA] content in specific embodiments.
Figure 8:
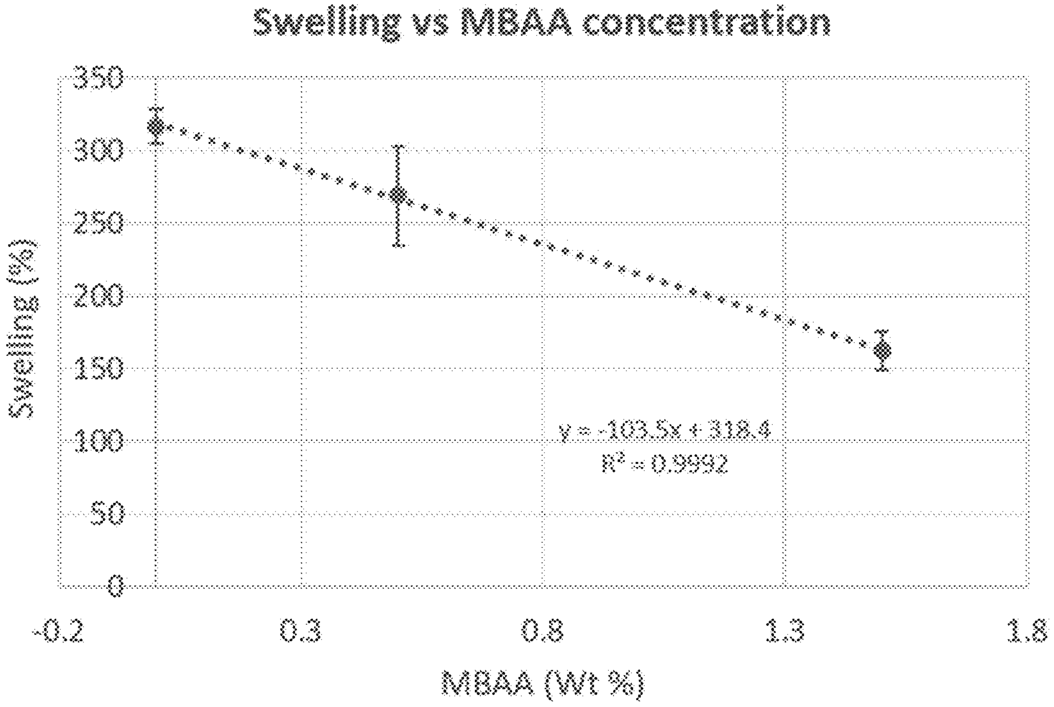
FIG. 8 shows specific embodiments of 25-35 PEGMEA formulation with and without N,N'-Methylenebisacrylamide.

FIG. 6 shows the swelling versus [HPA/HEA] content, and FIG. 7 shows swelling versus [HBA/HEA] content. As can be seen, control over the swelling can be achieved by varying the ratio of the hydrophobic and hydrophilic monomer content in the polymer.

Controlling Swelling with Short Crosslinkers N,N'-Methylenebisacrylamide (MBAA)

A 25-35 PEGMEA formulation without additional crosslinkers and with varying amounts of MBAA were synthesized. The compositions used were as follows.

| 25-35 PEGMEA | | +0.5% MBAA | |
|---|---|---|---|
| Reagents | Wt (%) | Reagents | Wt (%) |
| 55 wt/vol % PEGDA3.4K | 1-2 | 55 wt/vol % PEGDA3.4K | 1-2 |
| PEGMEA | 25-35 | PEGMEA | 25-35 |
| $DIH_2O$ | 40-45 | $DIH_2O$ | 40-45 |
| 4 wt/vol % LAP | 20-30 | 4 wt/vol % LAP | 20-30 |
| 3 wt/vol % UV | 1-5 | 3 wt/vol % UV | 1-5 |
| | 100 | MBAA | 0.5 |
| | | | 100 |

| +1.5% MBAA | |
|---|---|
| Reagents | Wt (%) |
| 55 wt/vol % PEGDA3.4K | 1-2 |
| PEGMEA | 25-35 |
| $DIH_2O$ | 40-45 |
| 4 wt/vol % LAP | 20-30 |
| 3 wt/vol % UV | 2-3 |
| MBAA | 1.5 |
| | 100 |

As shown in FIG. 8, 25-35 PEGMEA formulation without additional crosslinkers swelled up to 316.73%. Adding 0.5% MBAA decreased swelling by 47.6%, and adding an additional 1% MBAA decreased swelling by 106.8%.

While the disclosure has been described with reference to the specific embodiments thereof, it should be understood by those skilled in the art that various changes may be made and equivalents may be substituted without departing from the true spirit and scope of the disclosure as defined by the appended claim(s). In addition, many modifications may be made to adapt a particular situation, material, composition of matter, method, operation or operations, to the objective, spirit and scope of the disclosure. All such modifications are intended to be within the scope of the claim(s) appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations is not a limitation of the disclosure.

What is claimed is:

1. A printable composition comprising:

about 1 weight percent (wt %) to about 40 wt % of one or more hydrophilic monomers;

a swelling control agent selected from a monomer that is hydrophobic relative to the one or more hydrophilic monomers, or a combination of a short chain cross-linker and a monomer that is hydrophobic relative to the one or more hydrophilic monomers;

about 0.01 wt % to about 2 wt % of a photo initiator; and 0 wt % to about 75 wt % of a vehicle comprising a protic solvent, by weight of the printable composition;

wherein the hydrophilic monomer comprises one or more of hydroxy $C_{1-2}$ alkyl (meth)acrylates, poly(alkylene oxide) alkyl ether (meth)acrylates, N-hydroxy $C_{1-2}$ alkyl (meth)acrylamides, or mixtures thereof;

wherein the monomer that is hydrophobic relative to the one or more hydrophilic monomers comprises hydroxypropyl acrylate (HPA); and the short chain crosslinkers comprise poly(alkylene oxide) di(meth)acrylates having a weight average molecular weight (Mw) of about 400 to about 20,000, diethylene glycol di(meth)acrylate, tetraethylene glycol di(meth)acrylate, N,N'-methylenebis(acrylamide), (poly)lactic acid di(meth)acrylate, (poly)glycolic acid di(meth)acrylate, (poly)lactic-coglycolide di(meth)acrylate, (poly)caprolactone di(meth)acrylate, (poly)dioxanone di(meth)acrylate, (poly)fumarate di(meth)acrylate, (carboxy)(methyl)cellulose di(meth)acrylate, hyaluronic acid di(meth)acrylate, heparan sulfate di(meth)acrylate, dextran di(meth)acrylate, alginate di(meth)acrylate, pectin di(meth)acrylate, or collagen di(meth)acrylate or mixtures thereof;

provided that when the swelling control agent is a monomer that is hydrophobic relative to the one or more hydrophilic monomers, then the printable composition has a weight ratio of the hydrophilic monomer to the monomer that is hydrophobic relative to the hydrophilic monomer of about 3:1 to about 1:3; and when the swelling control agent comprises a short chain crosslinker then the printable composition comprises about 0.01 wt % to about 5 wt % of the short chain crosslinker.

2. The printable composition of claim 1 wherein the hydrophilic monomer comprises one or more of poly(ethylene glycol) methyl ether acrylate (PEGMEA), poly(ethylene glycol) methyl ether methacrylate, poly(propylene glycol) methyl ether acrylate, poly(propylene glycol) methyl ether methacrylate, hydroxyethyl acrylate (HEA), N-hydroxyethyl acrylamide (HEAA), or mixtures thereof.

3. The printable composition of claim 1 wherein the one or more hydrophilic monomers are selected from the group consisting of PEGMA, HEA, and mixtures thereof.

4. The printable composition of claim 1 wherein the printable composition comprises about 5 wt % to about 35 wt % of the one or more hydrophilic monomers.

5. The printable composition of claim 1 wherein the printable composition comprises (a) HPA and (b) HEA present in a weight ratio between (a) and (b) of about 3:1 to about 1:3.

6. The printable composition of claim 1, wherein the poly(alkylene oxide) di(meth)acrylate comprises poly(ethylene glycol) diacrylate.

7. The printable composition of claim 1 wherein the printable composition comprises about 0.5 wt % to about 3 wt % of the short chain crosslinkers.

8. The printable composition of claim 1 wherein the photo initiator comprises lithium phenyl-2,4,6-trimethylbenzoylphosphinate (LAP), Trimethylbenzoyl based photoinitiators, diphenyl(2,4,6-trimethylbenzoyl)phosphine oxide (TPO nanoparticle) ruthenium, and riboflavin, or mixtures thereof.

9. The printable composition of claim 1 wherein the printable composition further comprises one or more additives comprising polymers, UV dyes, natural extracellular matrices, photoinitiators, Peptides, amino acids, growth factors, denature extracellular matrices, extracellular matrix fragments or mixtures thereof.

10. The printable composition of claim 1 wherein the protic solvent comprises water, polyethylene glycol, Glycol diacrylate derivatives or mixtures thereof.

11. A method of preparing a three-dimensional article comprising printing a printable composition according to claim 1 to fabricate the three-dimensional article.

12. The method of claim 11, wherein the printing fabricates a three-dimensional article of an organ, wherein the organ is a mammalian organ.

13. The method of claim 11 wherein the printing comprises ink jet printing, extrusion printing, or layer-by-layer printing.

14. The method of claim 11 wherein the three-dimensional article has a swelling percentage of less than about 300% by weight, based on the non-hydrated weight of the three-dimensional article.

15. A method of manufacturing a three-dimensional article comprising: depositing a layer of a printable composition to a surface to obtain a deposited layer; irradiating the deposited layer; and repeating the depositing and irradiating steps until the deposited layers form the three-dimensional article;

wherein the printable composition comprises:

about 1 weight percent (wt %) to about 40 wt % of one or more hydrophilic monomers;

a swelling control agent selected from a monomer that is hydrophobic relative to the one or more hydrophilic monomers, or a combination of a short chain crosslinker and a monomer that is hydrophobic relative to the one or more hydrophilic monomers;

about 0.01 wt % to about 2 wt % of a photo initiator; and 0 wt % to about 75 wt % of a vehicle comprising a protic solvent, by weight of the printable composition;

wherein the hydrophilic monomer comprises one or more of hydroxy C1-2 alkyl (meth)acrylates, poly (alkylene oxide) alkyl ether (meth)acrylates, N-hydroxy C1-2 alkyl (meth)acrylamides, or mixtures thereof;

wherein the monomer that is hydrophobic relative to the one or more hydrophilic monomers comprises hydroxypropyl acrylate (HPA), and the short chain crosslinkers comprise poly(alkylene oxide) di(meth)acrylates having a weight average molecular weight (Mw) of about 400 to about 20,000, diethylene glycol di(meth)acrylate, tetraethylene glycol di(meth)acrylate, N,N'-methylenebis (acrylamide), (poly)lactic acid di(meth)acrylate, (poly)glycolic acid di(meth)acrylate, (poly)lactic-coglycolide di(meth)acrylate, (poly)caprolactone di(meth)acrylate, (poly)dioxanone di(meth)acrylate, (poly)fumarate di(meth)acrylate, (carboxy)(methyl) cellulose di(meth)acrylate, hyaluronic acid di(meth) acrylate, heparan sulfate di(meth)acrylate, dextran di(meth)acrylate, alginate di(meth)acrylate, pectin di(meth)acrylate, or collagen di(meth)acrylate or mixtures thereof;

provided that when the swelling control agent is a monomer that is hydrophobic relative to the one or more hydrophilic monomers, then the printable composition has a weight ratio of the hydrophilic monomer to the monomer that is hydrophobic relative to the one or more hydrophilic monomers of about 3:1 to about 1:3; and when the swelling control agent is a short chain crosslinker then the printable composition comprises about 0.01 wt % to about 5 wt % of the short chain crosslinkers.

16. The method of claim 15 wherein the deposited layer is irradiated at a wavelength from about 365 nm to about 405 nm.

* * * * *